United States Patent [19]

Nemoto et al.

[11] Patent Number: 5,002,756

[45] Date of Patent: Mar. 26, 1991

[54] METHOD FOR RELIEVING RADIOGENIC OR DRUG-INDUCED SIDE EFFECTS

[75] Inventors: Kyuichi Nemoto, Tokyo; Tetsushi Saino, Yono; Tomio Takeuchi, Tokyo; Teruya Nakamura, Kusatsu, all of Japan

[73] Assignee: Zaidanhojin Biseibutsu Kagakukenkyukai, Tokyo, Japan

[21] Appl. No.: 325,372

[22] Filed: Mar. 17, 1989

[30] Foreign Application Priority Data

Apr. 4, 1988 [JP] Japan .................................. 63-81315

[51] Int. Cl.$^5$ ..................... A61K 49/00; A61K 43/00; A61K 41/00
[52] U.S. Cl. ...................................... 424/10; 424/1.1; 424/90
[58] Field of Search .................... 424/10, 90; 564/157, 564/159, 201; 548/342

[56] References Cited

U.S. PATENT DOCUMENTS 4,525,299  6/1985  Umezawa et al. .................. 564/159
4,603,015  7/1986  Umeda et al. ....................... 564/201

FOREIGN PATENT DOCUMENTS 0188821  12/1985  European Pat. Off. .
207214   3/1986   Japan .

OTHER PUBLICATIONS

Chemical Abstracts, (vol. 108:210203t), 1988.

Primary Examiner—Stanley J. Friedman
Assistant Examiner—Kevin Weddington
Attorney, Agent, or Firm—Henry C. Nields

[57] ABSTRACT

An agent for relieving radiogenic or drug-induced side effects, characterized by comprising a spergualin derivative of the following formula (I):

$$NH_2—C(=NH)—NH—R_1—R_2—CONH—R_3—CONH—(CH_2)_4—NH—(CH_2)_3—NH—X$$

wherein $R_1$ represents $—(CH_2)_4—$, $—(CH_2)_6—$ $$-\!\!\left\langle\!\bigcirc\!\right\rangle\!\!-CH_2-,\ -\!\!\left\langle\!\bigcirc\!\right\rangle\!\!-(CH_2)_2-\ or$$

$$-CH_2-\!\!\left\langle\!\bigcirc\!\right\rangle\!\!-,$$

$R_2$ represents $—(CH_2)_2—$ or $—CH=CH—$,
$R_3$ represents $—(CH(OH)—CH(OMe)—$, $—CH_2—$ or $—(CH_2)_m—CH(OH)—(CH_2)_n—$ (m represent an integer of 0,1 or 2 and n represents an integer of 1 or 2)
X represents a hydrogen atom or a group formed by removing a hydroxyl group from a carboxyl group of an amino acid, or a pharmacologically acceptable salt thereof as an active ingredient.

2 Claims, No Drawings

METHOD FOR RELIEVING RADIOGENIC OR DRUG-INDUCED SIDE EFFECTS

BACKGROUND OF THE INVENTION

1. Prior Arts

Spergualin is a compound isolated from a culture filtrate of a spergualin-producing bacterium belonging to the genus Bacillus by Umezawa et al. and represented by the following formula:

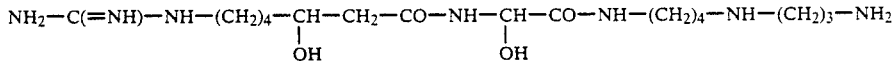

This compound is expected to be useful as an antimalignant tumor agent, since it is effective in the treatment of mouse leukemia L1210, mouse leukemia EL-4, Ehrlich carcinoma and sarcoma 180 (cf. U.S. Pat. No. 4,416,899).

As the results of the subsequent studies, there have been synthesized a number of spergualin derivatives, including those to be used in the present invention, having an improved anti-tumor activity or an elevated stability (cf. U.S. Pat. Nos. 4,518,532, 4,529,549, 4,556,735, EP 241797). It has been further disclosed that these compounds have an intense immunosuppressive effect (cf. EP-A$_2$-18592).

Thus they are expected to be effective as an immunosuppressive agent in organ transplantation or in the treatment of autoimmune diseases.

2. Problems to be Solved by the Invention

Chemotherapy and radiotherapy have been widely applied to the treatment of various diseases. However these therapeutics would frequently cause serious side effects, which makes it unavoidable to stop the treatment.

Therefore it is highly valuable to prevent or relieve the side effects caused by these therapeutics. However there has been known no agent capable of relieving the side effects caused by chemotherapy or radiotherapy.

SUMMARY OF THE INVENTION

1. Field of Industrial Application

This invention relates to a method for relieving radiogenic or drug-induced side effects which comprises administering a spergualin derivative as an active ingredient.

2. Means for Solving the Problems

The present invention relates to a method for relieving radiogenic or drug-induced side effects against a mammal characterized by administering a spergualin derivative of the following general formula (I), referred as the compound of the present invention hereinafter, as an active ingredient.

More particularly, it relates to a method for relieving radiogenic or drug-induced side effects against a mammal including human, characterized by adminstering a spergualin derivative of the following general formula (I):

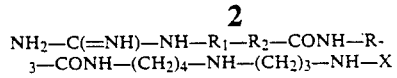

wherein $R_1$ represents $-(CH_2)_4-$, $-(CH_2)_6-$,

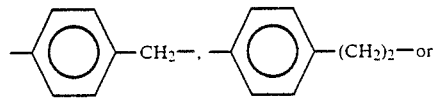

$R_2$ represents $-(CH_2)_2-$ or $-CH=CH-$,
$R_3$ represents $-CH(OH)-$, $-CH(OMe)-$, $-CH_2-$ or
$-(CH_2)_m-CH(OH)-(CH_2)_n-$ (m represents an integer of 0.1 or 2 and n represents an integer of 1 or 2)
X represents a hydrogen atom or a group formed by removing a hydroxyl group from a carboxyl group of an amino acid,
and a pharmacologically acceptable salt thereof as an active ingredient in an effective amount to the said mammal and thereafter starting chemotherapy or radiotherapy.

Among the compounds of the general formula (I), wherein $R_1$ is $-(CH_2)_4-$ or $-(CH_2)_6$, $R_2$ is $-(CH_2)_2-$, $R_3$ is $-CH(OH)-$, $-CH(OCH_3)-$, $-CH_2-$ or $-CH(CH_2OH)$ (conformation: S-form), and X is a hydrogen atom, are preferable as an active ingredient. When $R_3$ is a group other than $-CH(OH)-$, X may be a group which is formed by removing a hydroxyl group from a carboxyl group of an amino acid.

When $R_1$ is

and $R_2$ is $-(CH_2)_2-$, $R_3$ may be $-CH_2-$ or $-CH(CH_2-OH)-$ (conformation: S-form) and X may be a group formed by removing a hydroxyl group from a carboxyl group of an amino acid.

When $R_1$ is $-(CH_2)_4-$ or $-(CH_2)_6-$ and $R_2$ is $-CH=CH-$(trans-form), $R_3$ may be, for example, $-CH(OH)-$ or $-CH(OCH_3)-$.

Table 1 shows examples of compounds available as an active ingredient in the present invention.

TABLE 1

Chemical structures of the representative examples of the compound of the invention
$NH_2-C(=NH)-NH-R_1-R_2-CONH-R_3-CONH-(CH_2)_4-NH-(CH_2)_3-NH-X$

| | $R_1$ | $R_2$ | $R_3$ | X |
|---|---|---|---|---|
| 1 | $-(CH_2)_4-$ | $-(CH_2)_2-$ | $-CH(OH)-$ | H |

TABLE 1-continued

Chemical structures of the representative examples of the compound of the invention
$NH_2-C(=NH)-NH-R_1-R_2-CONH-R_3-CONH-(CH_2)_4-NH-(CH_2)_3-NH-X$

| | $R_1$ | $R_2$ | $R_3$ | X |
|---|---|---|---|---|
| 2 | $-(CH_2)_4-$ | $-(CH_2)_2-$ | $-CH(OCH_3)-$ | H |
| 3 | $-(CH_2)_6-$ | $-(CH_2)_2-$ | $-CH(OH)-$ | H |
| 4 | $-(CH_2)_4-$ | $-(CH_2)_2-$ | $-CH_2-$ | H |
| 5 | $-(CH_2)_4-$ | $-(CH_2)_2-$ | $(S)-CH(CH_2OH)$ | H |
| 6 | 4-C₆H₄-CH₂- | $-(CH_2)_2-$ | $-CH_2-$ | H |
| 7 | 4-C₆H₄-CH₂- | $-(CH_2)_2-$ | $(S)-CH(CH_2OH)$ | H |
| 8 | $-CH_2-$C₆H₄- | $-(CH_2)_2-$ | $(S)-CH(CH_2OH)$ | H |
| 9 | 4-C₆H₄-$(CH_2)_2-$ | $-(CH_2)_2-$ | $(S)-CH(CH_2OH)$ | H |
| 10 | $-(CH_2)_4-$ | $-CH=CH-$ trans | $-CH(OCH_3)-$ | H |
| 11 | $-(CH_2)_6-$ | $-CH=CH-$ trans | $-CH(OH)-$ | H |
| 12 | $-(CH_2)_4-$ | $-(CH_2)_2-$ | $-CH(OCH_3)-$ | PhG |
| 13 | $-(CH_2)_4-$ | $-(CH_2)_2-$ | $-CH(OCH_3)-$ | Leu |
| 14 | $-(CH_2)_4-$ | $-(CH_2)_2-$ | $-CH(OCH_3)-$ | Phe |
| 15 | $-(CH_2)_4-$ | $-(CH_2)_2-$ | $-CH(OCH_3)-$ | Leu—Leu |
| 16 | $-(CH_2)_4-$ | $-(CH_2)_2-$ | $-CH_2-$ | PhG |
| 17 | $-(CH_2)_4-$ | $-(CH_2)_2-$ | $-CH_2-$ | Leu |
| 18 | $-(CH_2)_4-$ | $-(CH_2)_2-$ | $-CH_2-$ | Leu—Leu |
| 19 | $-(CH_2)_4-$ | $-(CH_2)_2-$ | $(S)-CH(CH_2OH)$ | PhG |
| 20 | $-(CH_2)_4-$ | $-(CH_2)_2-$ | $(S)-CH(CH_2OH)$ | Leu |
| 21 | $-(CH_2)_4-$ | $-(CH_2)_2-$ | $(S)-CH(CH_2OH)$ | Leu—Leu |
| 22 | 4-C₆H₄-CH₂- | $-(CH_2)_2-$ | $-CH_2-$ | PhG |
| 23 | 4-C₆H₄-CH₂- | $-(CH_2)_2-$ | $-CH_2-$ | Leu |
| 24 | 4-C₆H₄-CH₂- | $-(CH_2)_2-$ | $-CH_2-$ | Leu—Leu |
| 25 | 4-C₆H₄-CH₂- | $-(CH_2)_2-$ | $(S)-CH(CH_2OH)$ | PhG |
| 26 | 4-C₆H₄-CH₂- | $-(CH_2)_2-$ | $(S)-CH(CH_2OH)$ | Leu |
| 27 | 4-C₆H₄-CH₂- | $-(CH_2)_2-$ | $(S)-CH(CH_2OH)$ | Leu—Leu |

TABLE 1-continued

Chemical structures of the representative examples of the compound of the invention
$NH_2-C(=NH)-NH-R_1-R_2-CONH-R_3-CONH-(CH_2)_4-NH-(CH_2)_3-NH-X$

| | $R_1$ | $R_2$ | $R_3$ | X |
|---|---|---|---|---|
| 28 | $-(CH_2)_6-$ | $-(CH_2)_2-$ | $(S)-CH(CH_2OH)$ | PhG |
| 29 | $-(CH_2)_6-$ | $-(CH_2)_2-$ | $(S)-CH(CH_2OH)$ | Leu |
| 30 | $-(CH_2)_6-$ | $-(CH_2)_2-$ | $(S)-CH(CH_2OH)$ | Leu—Leu |
| 31 | $-(CH_2)_6-$ | $-(CH_2)_2-$ | $-CH_2-CH(OH)-CH_2-$ | H |

In the above Table, PhG represents $C_6H_5-CH(NH_2)-CO-$, Leu represents $(CH_3)_2CH-CH_2-CH(NH_2)-CO-$, Phe represents $C_6H_5-CH_2-CH(NH_2)-CO-$ and Leu-Leu represents

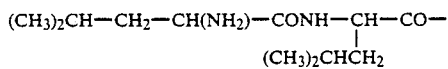

and their configuration involves D-, L- and DL-forms as well as a combination thereof.

The compound of the general formula (I) forms a salt together with an acid. Either an inorganic or an organic acid may be used in the formation of a salt, so long as it is pharmacologically acceptable. Examples of the inorganic acid include hydrochloric, sulfuric, nitric and phosphoric acids. On the other hand, examples of the organic acid include acetic, propionic, succinic, fumaric, maleic, malic, tartaric, glutaric, citric, benzensulfonic, toluenesulfonic, methanesulfonic, ethanesulfonic, propanesulfonic, aspartic and glutamic acids.

The compounds cited above are disclosed in U.S. Pat. Nos. 4,518,532, 4,529,549, 4,556,735, EP241797 and each can be synthesized by a known method. When the compound of the present invention is used as an agent for relieving radiogenic or drug-induced side effects, it may be administered in the form of, for example, an injection, an oral drug or a suppository either alone or as a mixture thereof with appropriate excipients or carrier(s).

The excipients or carriers may be selected from pharmacologically acceptable ones. The type and composition thereof may vary depending on the route or manner of the administration. Examples of liquid carriers include water, alcohols and animal, vegetable and synthetic oils such as soybean oil, olive oil and mineral oil. Examples of solid carriers include sugars such as maltose and sucrose, amino acids, cellulose derivatives such as hydroxypropylcellulose and organic acid salts such as magnesium stearate. When the compound of the present invention is to be formulated into an injection, physiological saline solution, various buffers, sugar solutions such as glucose, inositol, mannitol or lactose solutions and glycols such as ethylene glycol or polyethylene glycol may be preferably employed as a solvent. Alternately, the compound of the present invention may be lyophilized together with appropriate excipients or carriers, for example, sugars such as inositol, mannitol, lactose or sucrose or amino acids such as phenylalanine and the resulting lyophilized perparation may be dissolved in an solvent suitable for intravenous administration, for example, sterilized water, physiological saline solution, a glucose solution, an electrolyte solution or an amino acid solution at the use.

The amount of the compound of the present invention in a preparation may vary depending on the formulation manner. It usually amounts to about 0.1 to 100 % by weight, preferably about 1 to 98 % by weight, of the whole preparation. For example, an injection may usually contain about 0.1 to 30 % by weight, preferably about 1 to 10 % by weight, of the active ingredient and about 99.1 to 70 % by weight, preferably about 99 to 90 % by weight of carriers or ercipients. When the compound of the present invention is to be orally administered, it may be formulated into, for example, a tablet, a capsule, powder, granules, a solution or a dry syrup, together with the above-mentioned solid or liquid carrier(s). The capsule, tablet or granules may usually contain about 5 to 100 % by weight, preferably about 25 to 98 % by weight, of the active ingredient.

The compound of the present invention is administered before starting chemotherapy or radiotherapy. The administration of the compound of the present invention is usually started within about ten days, preferably about 5-3 days before the start of chemotherapy or radiotherapy and may be continued till the day on which the chemotherapy or the radiotherapy is started or finished.

The dose of the compound of the present invention may vary depending on the age, body weight, sex and condition of the subject as well as the purpose of the treatment. Generally speaking, it may be parenterally administered in a dose of 1 to 100 mg/kg/day or orally administered in a dose of 5 to 1000 mg/kg/day.

(Effect of the Compound of the Invention)

The present inventors have examined the physiological activities of the compound of the present invention and consequently found that it can relieve the side effects of anticancer agents having bone marrow toxicity. Further studies on the protective effects of the compound of the present invention on damages induced by radiation have revealed that a mammal, to which the compound of the present invention have been preliminarily administered, is resistant against irradiation at a lethal dose.

These results indicate that the compound of the present invention is useful in relieving organ damages, especially bone marrow damage, caused by anticancer agents or irradiation.

Now the effects of the compound of the present invention will be illustrated in detail.

TEXT EXAMPLE 1

Effect of the compound of the present invention in suppressing the killing effect of anticancer agent on spleen colony forming cells.

6 mg/kg of the compound 1 or physiological saline solution was intra-peritoneally administered to a female C3H mouse repeatedly for seven days. On the final day of the administration, various anticancer agents were intravenously injected to the animals once. On the next day of the final administration, bone marrow cells of each animal were collected. Then $1 \times 10^5$ or $5 \times 10^4$ bone marrow cells thus obtained were intravenously injected into another mouse of the same strain which had been systemically irradiated with 950 rad of X-ray. Seven days after the transplantation of the bone marrow cells, the spleen of each mouse was fixed with a Bouin's fluid and colonies on the surface of the spleen were counted. As shown in Table 2, the compound 1 significantly suppressed the effect of every tested anticancer agent in killing the spleen colony forming cells.

TABLE 2

Effect of the compound of the invention in suppressing the killing effects of various carcinostatic agents on spleen colony forming cells

| Test group | No. of spleen colonies (mean ± SD) |
|---|---|
| Test 1: | |
| physiological saline soln. | 18 ± 3 |
| physiological saline soln. + mitomycin (3 mg/kg) | 4 ± 3 (p <0.01) |
| compound 1 + micomycin (3 mg/kg) | 10 ± 2 |
| Test 2: | |
| physiological saline soln. | 36 ± 2 |
| physiological saline soln. + cyclophosphamide (200 mg/kg) | 7 ± 3 (p <0.05) |
| compound 1 + cyclophosphamide (200 mg/kg) | 13 ± 5 |
| Test 3: | |
| physiological saline soln. | 34 ± 7 |
| physiological saline soln. + 5-fluorouracil (65 mg/kg) | 13 ± 5 (p <0.01) |
| compound 1 + 5-fluorouracil (65 mg/kg) | 38 ± 4 |

No. of transplanted bone marrow cells:
Test 1: $5 \times 10^4$; and
Tests 2 to 4: $1 \times 10^5$.

TEXT EXAMPLE 2

Radiation protective effect of the compound of the invention.

6 mg/kg of the compound 1 was intra-peritoneally administered to a female CBA mouse repeatedly for three to seven days. On the other hand, physiological saline solution was administered to a control group. On the next day of the final administration, each animal was sytemically irradiated with 850 rad of X-ray.

Table 3 shows that a significant surviving effect is observed in the test group on every administration schedule.

TABLE 3

Radiation protective effect of the compound of the invention

| Test group | Administration (days) | Median surviving period (days) | Significant difference* |
|---|---|---|---|
| Control (physiological saline soln.) | | 11.6 (9 to 12) | |
| Compound 1 | −7 to −1 | 12.6 (9 to 15) | p <0.05 |
| | −5 to −1 | 12.4 (11 to 14) | p <0.01 |
| | −5 to −1 | 13.6 (10 to >30) | p <0.01 |

*: Mann-Whiteney U-test.

To further illustrate the present invention, the following Examples will be given.

TEST EXAMPLE 3

Radiation protective effect of the compound of the invention 12 mg/kg of the compound 1 was intra-peritoneally administered to a male BALB/C mouse repeatedly for one to five days. On the other hand, physiological saline solution was administered to a control group. On the next day of the final administration, each animal was sytemically irradiated with 750 rad of X-ray.

Table 3 shows that a significant surviving effect is observed in the test group on every administration schedule.

TABLE 3

Radiation protective effect of the compound of the invention

| Administration (days before radiation) | Surviving period (days from radiation) | | | | | | | | | Significant difference* |
|---|---|---|---|---|---|---|---|---|---|---|
| Control | 10 | 10 | 11 | 11 | 12 | 12 | 12 | 13 | 13 | 14 | |
| −1, −2, −3, −4, −5 | 10 | 11 | 11 | 11 | 12 | 13 | 13 | 13 | 14 | 16 | |
| −1, −2, −3, −4 | 12 | 15 | 15 | 15 | 15 | 17 | 18 | 19 | >40 | >40 | P <0.001 |
| −1, −2, −3 | 14 | 14 | 14 | 15 | 16 | 23 | 28 | >40 | >40 | >40 | P <0.001 |
| −1, −2 | 3 | 10 | 12 | 13 | 13 | 14 | 15 | 31 | >40 | >40 | |
| −1 | 10 | 11 | 11 | 11 | 12 | 12 | 13 | 13 | 16 | >40 | |

*: Mann-Whiteney U-test

EXAMPLE 1

To 30 parts by weight of the hydrochloride of the compound 1 was added distilled water for injection to thereby give the total volume of 2000 parts. After dissolution, the resulting solution was aseptically filtered through a Millipore Filter GS-type. 2-g portions of the filtrate were introduced into 10-ml vials and lyophilized. Thus a lyophilized injection containing 30 mg of the hydrochloride of the compound 1 per vial was obtained.

EXAMPLE 2

50 parts by weight of the hydrochloride of the compound 2, 600 parts of milk sugar, 330 parts of crystalline cellulose and 20 parts of hydroxypropylcellulose were thoroughly mixed together, compressed with a roller compacter and then ground. The obtained particles were dressed through 16-mesh to 60-mesh sieves to thereby give granules.

EXAMPLE 3

30 parts by weight of the hydrochloride of the compound 22, 120 parts of crystalline milk sugar, 147 parts of crystalline cellulose and three parts of magnesium stearate were mixed together in a V-type mixer. The obtained mixture was tableted to thereby give tablets each weighing 300 mg.

We claim:

1. A method for relieving radiogenic or drug-induced side effects against a mammal, which comprises administering a spergualin derivative of the following formula (I):

NH$_2$—C(=NH)—NH—R$_1$—R$_2$—CONH—R$_3$—CONH—(CH$_2$)$_2$—NH—(CH$_2$)$_3$—NH—X wherein R$_1$ represents —(CH$_2$)$_4$—, (CH$_2$)$_6$—,

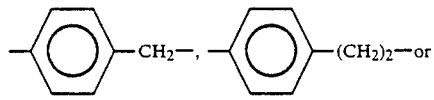

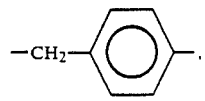

R$_2$ represents —(CH$_2$)$_2$— or —CH=CH—,
R$_3$ represents —CH(OH)—, —CH(OMe)—, —CH$_2$— or —(CH$_2$)$_m$—CH(OH)—(CH$_2$)$_n$— (m represents an integer of 0.1 or 2 and n represents an integer of 1 or 2) X represents a hydrogen atom or a group formed by removing a hydroxyl group from a carboxyl group of an amino acid, and a pharmacologically acceptable salt thereof in a therapeutically effective amount to the said mammal and thereafter starting chemotherapy or radiotherapy.

2. The method of claim 1, in which the spergualin derivative is a following compound.

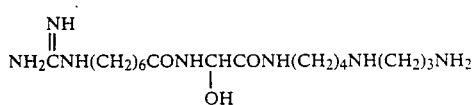

or a pharmacologically acceptable salt thereof.

* * * * *